(12) United States Patent
Pickens et al.

(10) Patent No.: US 7,857,990 B2
(45) Date of Patent: Dec. 28, 2010

(54) CALCIUM HYPOCHLORITE COMPOSITION

(75) Inventors: Stanley R. Pickens, Monroeville, PA (US); Timothy A. Okel, Trafford, PA (US); Erik A. Schoenman, Gibsonia, PA (US); Shantilal M. Mohnot, Murrysville, PA (US); Patrick Ryan, Buchanan, TN (US)

(73) Assignee: PPG Industries Ohio, Inc., Cleveland, OH (US)

( * ) Notice: Subject to any disclaimer, the term of this patent is extended or adjusted under 35 U.S.C. 154(b) by 506 days.

(21) Appl. No.: 11/847,724

(22) Filed: Aug. 30, 2007

(65) Prior Publication Data
US 2008/0067468 A1 Mar. 20, 2008

Related U.S. Application Data

(60) Provisional application No. 60/826,243, filed on Sep. 20, 2006.

(51) Int. Cl.
*C01B 11/06* (2006.01)

(52) U.S. Cl. .................. 252/187.28; 252/187.27; 252/186.25; 422/37

(58) Field of Classification Search ......... 252/186.25, 252/187.25, 187.27, 187.28; 422/37
See application file for complete search history.

(56) References Cited

U.S. PATENT DOCUMENTS

| | | | | |
|---|---|---|---|---|
| 3,953,354 | A * | 4/1976 | Faust | 252/186.37 |
| 4,035,484 | A * | 7/1977 | Faust et al. | 424/665 |
| 4,053,429 | A * | 10/1977 | Tatara et al. | 252/187.28 |
| 4,108,792 | A * | 8/1978 | Farmer et al. | 252/187.29 |
| 4,118,524 | A * | 10/1978 | Saeman | 427/213 |
| 4,692,335 | A * | 9/1987 | Iwanski | 424/665 |
| 4,741,858 | A * | 5/1988 | Choy et al. | 252/186.36 |
| 4,747,978 | A * | 5/1988 | Loehr et al. | 252/175 |
| 4,865,760 | A * | 9/1989 | Johnson et al. | 252/187.28 |
| 5,049,385 | A | 9/1991 | Wiedrich et al. | |
| 5,205,961 | A * | 4/1993 | Shenefiel et al. | 252/186.37 |
| 5,384,102 | A | 1/1995 | Ferguson et al. | |
| 5,427,748 | A | 6/1995 | Wiedrich et al. | |
| 5,801,262 | A | 9/1998 | Adams | |
| 5,908,660 | A | 6/1999 | Griffith et al. | |
| 5,919,298 | A | 7/1999 | Griffith et al. | |
| 5,936,031 | A | 8/1999 | Woodgate et al. | |
| 6,298,871 | B1 | 10/2001 | Pickens et al. | |
| 6,776,926 | B2 * | 8/2004 | Martin | 252/187.29 |
| 6,894,398 | B2 * | 5/2005 | Pon | 257/786 |
| 6,995,129 | B2 * | 2/2006 | Olson et al. | 510/379 |
| 7,153,438 | B2 * | 12/2006 | Souter et al. | 210/764 |
| 7,201,856 | B2 * | 4/2007 | Souter et al. | 252/181 |
| 7,431,863 | B2 * | 10/2008 | Pickens | 252/187.3 |
| 2003/0212228 | A1 | 11/2003 | Dai et al. | |
| 2004/0217326 | A1 * | 11/2004 | Souter et al. | 252/179 |
| 2005/0233900 | A1 * | 10/2005 | Smith et al. | 502/407 |
| 2006/0164029 | A1 * | 7/2006 | Suzuki et al. | 318/283 |
| 2007/0125979 | A1 * | 6/2007 | Lei et al. | 252/176 |

OTHER PUBLICATIONS

"Periodic Classification or Chart of the Elements", General Chemistry, Theodore L. Brown; 1963, Charles E. Merrill Books, Inc.

* cited by examiner

*Primary Examiner*—Joseph D Anthony
(74) *Attorney, Agent, or Firm*—Irwin M. Stein; Linda Pingitore

(57) ABSTRACT

Describes a composition comprising a mixture of (1) a major amount of calcium hypochlorite, e.g., hydrated calcium hypochlorite, and (2) a minor amount of calcium hypochlorite-compatible hydrophobic additive (other than discrete particulate Group IIA or IIIA metal stearates) in amounts sufficient to provide the composition with reduced hydrophilic properties. The composition has a solution rate in water at standard conditions that is less than the calcium hypochlorite used to prepare the composition, but sufficient for the intended application. Describes also calcium hypochlorite compositions in which the hydrophobic additive is an organosilicon material, or a metal oxide, e.g., amorphous precipitated silica, treated with a hydrophobizing agent, such as an organo-silicon material, e.g., an organo-silane and/or organo-siloxane material.

20 Claims, No Drawings

CALCIUM HYPOCHLORITE COMPOSITION

CROSS-REFERENCE TO RELATED APPLICATIONS

This application claims the benefit of priority from U.S. Provisional Patent Application No. 60/826,243, filed Sep. 20, 2006.

FIELD OF THE INVENTION

This invention relates to calcium hypochlorite compositions. In particular, this invention relates to calcium hypochlorite compositions having a reduced tendency to swell when in contact with water.

BACKGROUND OF THE INVENTION

Residential and commercial water systems, e.g., residential waste water treatment systems and evaporative cooling towers for air conditioning, are subject to contamination from the presence and growth of microbes, e.g., algae, pathogenic bacteria and fungi. The sanitization of such water systems including, but not limited to, recirculating water systems, often involves introducing a hypochlorite anion donor material, such as calcium hypochlorite, into the water system so as to establish a desired level, e.g., a sanitizing amount, of free available chlorine (FAC) within the water system. The presence of free available chlorine serves to eradicate or control deleterious amounts of undesirable microbial species that are found in the water comprising the water system, the existence of which microbial species can lead to the development of infection or disease in humans and animals.

Free available chlorine (FAC) can be established and maintained in such water systems by adding regularly a source of hypochlorous acid (HOCl) or hypochlorite anion (ClO$^-$), e.g., calcium hypochlorite or an aqueous solution of calcium hypochlorite, to the water. FAC levels of from 1 to 45, e.g., from 1 to 10 parts per million parts of water (ppm), sometimes reported as milligrams per Liter (mg/L), are commonly maintained in recreational water systems. FAC levels of 1 ppm or less, e.g., 0.5 to 1 ppm, are commonly maintained in cooling water systems. Water having a FAC content in amounts of greater than 10 ppm (generally in the range of hundreds to thousands of mg/L) can be used to sanitize surfaces or articles to which it is applied, e.g., food, equipment and tables used for the processing of raw food or in the preparation of processed food products.

Hypochlorous acid or hypochlorite anion can be introduced into water by passing the water through an apparatus (often referred to as a feeder), e.g., a container having a canister that contains calcium hypochlorite material, which is usually in the form of granules, tablets or pellets. When water is introduced into such a container and into contact with the calcium hypochlorite within the canister, the calcium hypochlorite dissolves, thereby forming an aqueous solution comprising hypochlorite anion. This solution may be mixed with a water supply, added to water to be sanitized, or used directly for the intended application.

In some commercial applications, such as waste water or cooling tower applications, the container holding the calcium hypochlorite material may receive infrequent attention, e.g., monthly or for longer intervals. If the calcium hypochlorite material within the container is exposed to humid conditions for an extended length of time, the portion of the calcium hypochlorite not in direct contact with water can absorb water. In that circumstance, the solid calcium hypochlorite material, e.g., tablets of calcium hypochlorite, can become soft and swollen, and develop a consistency similar to mush. Such expanded calcium hypochlorite tablets may hang-up in the container, which can cause an upset in the amount and delivery rate of the aqueous solution comprising hypochlorous acid/hypochlorite anion. In some instances, the calcium hypochlorite within the container is consumed prematurely.

Minor amounts of discrete particulate Group IIA or IIIA (of the Periodic Chart of the Elements) metal stearates, e.g., calcium stearate or aluminum stearate, have been added to calcium hypochlorite to slow its dissolution in water and to minimize its absorption of water. However, such discrete Group IIA and IIIA metal stearates may cause problems in the production of metal stearate-calcium hypochlorite mixtures, particularly in the process of producing formed articles, e.g., tablets. For example, in the preparation of metal stearate-calcium hypochlorite mixtures, dust collectors are often used to collect airborne particles of calcium hypochlorite and metal stearate, thereby to maintain an environmentally safer and more pleasant working environment. The foregoing metal stearates, e.g., calcium stearate or aluminum stearate, are generally used in a finely-divided powdery form. Consequently, the metal stearate powder can become easily airborne, and is eventually collected in the dust collector and air ducts associated with the dust collector, where it can reach elevated concentrations, vis-à-vis, the concentration of the metal stearate in the calcium hypochlorite formed article. Because of the hot conditions and the elevated concentration of metal stearate in the calcium hypochlorite-metal stearate mixture that can exist in such dust collector equipment, the calcium hypochlorite in the dust collector equipment may become unstable. Consequently, it is desirable that the preparation of such mixtures be avoided.

It would, therefore, be advantageous to develop a solid calcium hypochlorite composition that has reduced hydrophilicity (affinity for water), vis-à-vis, commercial grades of unblended calcium hypochlorite, and the preparation of which solid composition does not have the aforedescribed production problems. It would also be desirable that such a solid calcium hypochlorite composition have a FAC content that is at least sufficient to allow its practical use for the batch and/or continuous sanitization of water systems, e.g., recirculating water systems such as evaporative cooling tower waters, evaporative condensers, residential waste water treatment systems, etc.

SUMMARY OF THE INVENTION

In accordance with a non-limiting embodiment of the present invention, there is provided a composition comprising a mixture of (1) a major amount of calcium hypochlorite, e.g., hydrated calcium hypochlorite, and (2) a minor amount of at least one calcium hypochlorite-compatible hydrophobic additive that is sufficient to provide a calcium hypochlorite composition having reduced hydrophilicity, said composition being substantially free of discrete particulate Group IIA or IIIA metal stearate. In a non-limiting embodiment, the solution rate in water of said calcium hypochlorite composition is less than the solution rate of the calcium hypochlorite used to prepare the calcium hypochlorite composition.

In another non-limiting embodiment of the present invention, the calcium hypochlorite-compatible hydrophobic additive is at least one hydrophobic metal oxide that is used in amounts sufficient to provide a calcium hypochlorite composition having reduced hydrophilic properties. In a further non-limiting embodiment of the present invention, the calcium hypochlorite-compatible hydrophobic additive is an organo-silicon material, e.g., an organo-silane materials or organo-siloxane material, which is used in amounts sufficient to provide a calcium hypochlorite composition having reduced hydrophilic properties.

DETAILED DESCRIPTION OF THE INVENTION

For purposes of this specification (other than in the operating examples), unless otherwise indicated, all numbers expressing quantities and ranges of materials, process conditions, etc are to be understood as modified in all instances by the term "about". Accordingly, unless indicated to the contrary, the numerical parameters set forth in this specification and attached claims are approximations that can vary depending upon the desired results sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Further, as used in this specification and the appended claims, the singular forms "a", "an" and "the" are intended to include plural referents, unless expressly and unequivocally limited to one referent.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurement, including that found in the measuring instrument. Also, it is to be understood that any numerical range recited in this specification is intended to include all sub-ranges subsumed therein. For example, a range of "1 to 10" is intended to include all sub-ranges between and including the recited minimum value of 1 and the recited maximum value of 10, i.e., a range having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

As used in the following description and claims, the following terms have the indicated meanings:

The term "calcium hypochlorite" means calcium hypochlorite having an unspecified amount of bound water or water of hydration, and includes hydrated calcium hypochlorite and dry calcium hypochlorite. The term "calcium hypochlorite" includes calcium hypochlorite that also contains inorganic salts, oxides and/or hydroxides that are incorporated into the calcium hypochlorite incidental to the calcium hypochlorite manufacturing process.

The term "hydrated calcium hypochlorite" means calcium hypochlorite having from 5.5 to 16 weight percent water, e.g., as bound water or as water of hydration. See, calcium hypochlorite, hydrated (UN #2880) in 49 CFR 172.101, Appendix A.

The term "dry calcium hypochlorite" means calcium hypochlorite having less than 5.5 weight percent water, e.g., as bound water or as water of hydration. See, calcium hypochlorite, dry (UN #1748) in 49 CFR 172.101, Appendix A.

The term "calcium hypochlorite-compatible" means a material that does not react chemically with solid calcium hypochlorite to any substantial degree at ambient conditions of temperature and pressure to form other identifiable chemical compounds, or that does not cause instability of the calcium hypochlorite with which it is blended, e.g., by lowering the self accelerating decomposition temperature (SADT) of the calcium hypochlorite. The term "calcium hypochlorite-compatible" does not exclude the formation of hydrogen or covalent bonds between the surface of solid calcium hypochlorite and the calcium hypochlorite-compatible material, e.g., an organo silicon material.

The term "discrete" as used for example in the phrase "discrete particulate Group IIA or Group IIIA metal stearate" means that the indicated material is a separate entity that is visually distinguishable (with or without magnification) from other materials with which it may be blended. The term discrete does not exclude materials, such as solid carriers, that may be coated or treated with another material, e.g., a metal oxide carrier that is treated with a metal stearate.

The term "hydrophilic" or "hydrophilicity" means having an affinity for water.

The term "hydrophobic" means lacking affinity for water. Hydrophobic materials will generally separate, e.g., float, when mixed with water that does not contain dispersant assisting additives, e.g., surfactant materials.

The term "hydrophobic additive" means a material that when applied to, e.g., coated on or mixed with, a hydrophilic material, such as calcium hypochlorite, provides reduced hydrophilic properties to the mixture of hydrophobic additive and hydrophilic material. The reduction in hydrophilic properties of the mixture may range from a partial or slight reduction in hydrophilic properties to a mixture that is completely hydrophobic, depending on the amount of hydrophobic additive applied to the hydrophilic material. In a non-limiting embodiment, the hydrophobic additive comprises an organic hydrophobizing reagent, such as an organo silicon material. In a further non-limiting embodiment, the hydrophobic additive comprises a metal oxide (carrier) that contains hydrophobizing agent (reagent) on its surface.

The term "metal oxide" means a solid metal oxide (hydrated or non-hydrated) that is non-flammable, and that contains hydrogen or hydroxyl groups on its surface, which groups are capable of bonding, e.g., covalently bonding, with an organic hydrophobizing agent. The term "metal oxide" includes inorganic metal oxides, mixed metal oxides, natural or synthetic clays, e.g., aluminosilicates; and materials having a core of one material and a coating of a metal oxide, e.g., a material comprising a core of a clay, titanium or aluminum oxide and a coating of a different metal oxide that contains hydrogen or hydroxyl groups on its surface, e.g., precipitated silicon dioxide, so that the material takes on the characteristics of the metal oxide comprising the coating. For purposes of the present description, silicon is considered to be a metal.

The term "major amount" means an amount of at least 50 weight percent.

The term "minor amount" means an amount of less than 50 weight percent.

The terms "mixture", "admixture", "blend" or terms of like import, as used for example in connection with a described mixture of calcium hypochlorite and hydrophobic additive means that the mixture, admixture or blend comprises a physical intermingling of the described materials. The physical intermingling includes, but is not limited to, particulate calcium hypochlorite coated (partially or completely) with the hydrophobic additive and/or particulate calcium hypochlorite blended with the hydrophobic additive. The terms "mixture", "admixture", "blend" or terms of like import includes formed articles, e.g., tablets or other shaped forms, prepared from such mixtures, admixtures or blends of calcium hypochlorite and one or more calcium hypochlorite-compatible hydrophobic additives.

The term "solid" means a physical state other than liquid or gaseous.

The term "solution rate" means the rate at which a solid material such as calcium hypochlorite or a mixture of for example calcium hypochlorite and hydrophobizing agent dissolves in water at a given temperature, e.g., 20° C. The solution rate is generally expressed in units of weight per unit of time, e.g., pounds per hour or grams per hour.

The term "Periodic Classification or Chart of the Elements" means the classification of the elements, as illustrated in the text General Chemistry by Theodore L. Brown, 1963, Charles E. Merrill Books, Inc., Columbus Ohio.

Calcium hypochlorite [CAS 7778-54-3] is a known and commercially available material. Commercial grades of calcium hypochlorite generally contain at least 39, e.g., at least 45 weight percent, free available chlorine. Some commercial grades of calcium hypochlorite contain at least 50 or 55 weight percent free available chlorine, and often contain at least 60 weight percent free available chlorine, e.g., between 60 or 65 and 80 percent free available chlorine (FAC). In a non-limiting embodiment of the present invention, calcium hypochlorite that may be used to prepare the herein described compositions can contain between 39 and 80 weight percent FAC. In alternate non-limiting embodiments, the calcium hypochlorite can contain between 45 and 80, 50 and 80, 65 and 80, or 65 and 76 weight percent of FAC. Calcium hypochlorite used to prepare the compositions of the present invention can contain an amount of FAC that may comprise a range that may vary between any of the recited FAC values.

Chemically, the remaining constituents of commercially available grades of calcium hypochlorite generally comprise varying amounts of water, and varying small amounts of by-product calcium and alkali metal salts incorporated into the calcium hypochlorite product as an incident to the manufacturing process. Such inorganic salts include, but are not limited to, sodium chloride, calcium chloride, calcium hydroxide, calcium carbonate and calcium chlorate.

Water generally comprises between 5.5 and 16 percent by weight of current commercially available high strength hydrated calcium hypochlorite, although amounts of less than 5.5 weight percent, e.g., less than 5 weight percent, may be present in dry calcium hypochlorite, e.g., 1 to 2 weight percent. In alternate non-limiting embodiments, water comprises 12 percent by weight or less, e.g., 10 percent by weight or less and often 8.5 percent by weight or less, of commercially available calcium hypochlorite. In alternate non-limiting embodiments, the amount of water present in commercial grades of hydrated high strength calcium hypochlorite may range between 5.5 and 10 percent, such as between 5.5 and 8.5, e.g., between 6.5 and 7.5 percent, by weight of the calcium hypochlorite material. The amount of water that is present in calcium hypochlorite may comprise a range that may vary between any of the recited water values. Commercially available grades of calcium hypochlorite, e.g., such as the aforedescribed high strength hydrated calcium hypochlorite materials, may be used to prepare the calcium hypochlorite compositions of the present invention. Calcium hypochlorite is a hydrophilic material and dissolves in water. It has a reported solubility in water at 25° C. of 21.4%.

The particle size and particle size distribution of current commercially available calcium hypochlorite can vary, e.g., it can vary from a powder to a granular material. As a general guideline, commercially available granular calcium hypochlorite has a principal size distribution between 100 and 6 mesh, as measured by the American Standard Test Method E11 Alternative Sieve Designation (ASTM E11 ASD); namely, the particles vary in size principally between 0.15 millimeters (mm) (0.006 inches) and 3.35 mm (0.13 inches). In a non-limiting embodiment, particulate calcium hypochlorite can have a principal particle size distribution between 100 mesh (0.15 mm) and 10 mesh (1.8 mm), e.g., between 45 mesh (0.33 mm) and 14 mesh (1.17 mm), based on ASTM E11 ASD. Further, when solid formed articles of the calcium hypochlorite compositions of the present invention are prepared, one skilled in the art will select a particle size distribution for the calcium hypochlorite that is amenable to be compressed into the desired solid formed article, e.g., a tablet. A non-limiting example of commercially available granular calcium hypochlorite that can be used to prepare calcium hypochlorite compositions of the present invention is available from PPG Industries, Inc. under the trademark Pittclor®. Other non-limiting examples of granular calcium hypochlorite that can be used include calcium hypochlorite sold under the brand names, Induclor® 70, Zappit® 73 and Leslie'® Power Powder® Pro.

Calcium hypochlorite, as described herein, is typically present in the compositions of the present invention in a major amount. In a non-limiting embodiment, the calcium hypochlorite is present in the compositions of the present invention in an amount of at least 75 weight percent, e.g., at least 80 weight percent. In alternate non-limiting embodiments, the calcium hypochlorite is present in the compositions of the present invention in amounts of at least 85 weight percent, such as at least 90 weight percent, e.g., 95 to 99.5 weight percent. The calcium hypochlorite may be present in the compositions of the present invention in amounts that may range between any of the previously recited values.

Alternatively, the calcium hypochlorite may be present in the compositions of the present invention in amounts sufficient to provide at least 39% by weight FAC, such as at least 45% by weight FAC, e.g., at least 50 or 65% by weight FAC, based on the total weight of the composition. In a further non-limiting embodiment, the calcium hypochlorite is present in the composition in amounts that provide less than approximately 80% by weight FAC, e.g., less than 76% by weight FAC, based on the total weight of the composition. Compositions prepared in accordance with the present invention may have present therein calcium hypochlorite in an amount sufficient to provide an FAC content ranging between any of those recited values, e.g., between 65 and 76% by weight FAC.

In accordance with a non-limiting embodiment of the present invention, a minor amount of at least one hydrophobic additive, e.g., an organic hydrophobizing agent, is commingled with hydrophilic calcium hypochlorite. The amount of hydrophobic additive commingled with the calcium hypochlorite is sufficient to provide the resultant mixed product composition with reduced hydrophilic properties. In a further non-limiting embodiment of the present invention, the amount of hydrophobic additive commingled with the hydrophilic calcium hypochlorite is sufficient to lower the solution rate in water of the resulting calcium hypochlorite composition when measured at ambient conditions, i.e., the calcium hypochlorite composition has a solution rate at ambient temperature, e.g., 20° C. that is less than the solution rate of the hydrophilic calcium hypochlorite used to prepare the composition, but sufficient for use in the intended application.

In a non-limiting embodiment, the solution rate in water of the calcium hypochlorite composition is diminished to not more than 50 to 70 percent of the solution rate of the calcium hypochlorite used to prepare the composition. Measurement of the respective calcium hypochlorite solution rates is performed on calcium hypochlorite that has the same physical form, density, etc. For example, the solution rate in water of a calcium hypochlorite tablet that is free of hydrophobic additive is compared to a substantially similar calcium hypochlorite tablet that contains a hydrophobic additive, e.g., the tablets are formed by a substantially similar tableting process and have a substantially similar density, size, etc.

In a non-limiting embodiment of the present invention, the amount of hydrophobic additive that is commingled with the calcium hypochlorite is not more 25 weight percent, e.g., not more than 20 weight percent, based on the total weight of the composition. In alternate non-limiting embodiments, the amount of hydrophobic additive that is commingled with the calcium hypochlorite is not more than 15 percent, such as not more than 10 weight percent, e.g., 0.1 to 5 weight percent, based on the total weight of the composition. In a further non-limiting embodiment, the amount of hydrophobic additive is not more than 2 weight percent, such as from 0.1 to 2 weight percent, based on the total weight of the composition. In a still further non-limiting embodiment, the amount of hydrophobic additive is not more than 1 weight percent, such as from 0.1 to 0.5, e.g., from 0.15 to 0.3 or 0.15 to 0.25, weight percent, based on the total weight of the composition. The hydrophobic additive may be present in the compositions of the present invention in amounts that range between any of the previously recited values.

In accordance with a non-limiting embodiment of the present invention, the composition comprising commingled calcium hypochlorite and hydrophobic additive is substantially free of discrete particulate Group IIA and/or Group IIIA metal stearate. As discussed, such metal stearates, e.g., calcium and/or aluminum stearate, may pose production difficulties during the manufacture of metal stearate-containing calcium hypochlorite articles, e.g., tablets.

The hydrophobic additive used to prepare the calcium hypochlorite compositions of the present invention can vary. In accordance with a non-limiting embodiment of the present invention, the hydrophobic additive is substantially free of sulfur-containing groups. In another non-limiting embodiment, the organic portion of an organic hydrophobic additive may be oxidizable, e.g., it may be oxidized by oxygen released by decomposing calcium hypochlorite, although that is not a desired characteristic. In a still further non-limiting embodiment of the present invention, the hydrophobic additive is a food grade material; namely, it can be used for the treatment (direct and indirect) of food intended for human and animal consumption.

In a non-limiting embodiment, the hydrophobic additive is an organo-metallic material, e.g., an organo-silicon material, an organo-titanium material or an organo-zirconium material. In alternate non-limiting embodiments, the organo-silicon material is chosen from at least one of organo-silane materials and organo-siloxane materials. The organo-metallic reactant material may be represented by one of the following general formulae:

     I

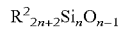     II

     III

     IV wherein (a) M is independently chosen from silicon, titanium or zirconium; (b) each $R^1$ is independently chosen from a saturated hydrocarbon group, e.g., a saturated aliphatic, cycloaliphatic or aromatically unsaturated hydrocarbon group, that contains from 1 to 18 carbon atoms; (c) each X is independently chosen from alkoxy containing from 1 to 12 carbon atoms, or acyloxy containing from 1 to 12 carbon atoms; (d) a is a number chosen from 1 to 4, (e) each $R^2$ is independently chosen from halo, hydroxy, or $R^1$ with the proviso that at least 50 mole percent of the $R^2$ substituents are saturated hydrocarbon groups; (f) n is a number of from 2 to 10,000; (g) m is a number of from 3 to 20, (h) $R^3$ is chosen from an aliphatic, cycloaliphatic, or aryl hydrocarbon containing from 1 to 6 carbon atoms, e.g., methyl, ethyl, propyl, butyl, hexyl, cyclohexyl, vinyl, or phenyl, or a glycidoxy alkyl group, e.g., 3-glycidoxy propyl, and (i) p is a number chosen from 4 to 1000. In alternate non-limiting embodiments, the number of carbon atoms in the saturated hydrocarbon groups represented by $R^1$ and $R^2$ may range from 1 to 12 carbon atoms, such as from 1 to 8 carbon atoms, e.g., 1 to 4 carbon atoms such as methyl or ethyl; and the number of alkoxy or acyloxy groups represented by X may range from 1 to 8, e.g., 1 to 4, such as methoxy or ethoxy. The saturated hydrocarbon groups may contain small amounts of unsaturated hydrocarbon groups because the source of or the preparative methods used to produce some hydrocarbon groups results in the presence of small amounts of residual ethylenic unsaturation in the hydrocarbon group.

In general formula I, X may be halogen, e.g., fluorine, chlorine, bromine and iodine, when the organo halo silane compound, organo halo titanium compound or organo halo zirconium compound is a hydrophobizing agent that is used to treat a solid carrier, which treated carrier is used as the hydrophobic additive. Generally, organo chloro silane compounds are used as the hydrophobizing agent. Organo halo silicon compounds, organo halo titanium compounds and organo halo zirconium compounds can react directly with water to produce hydrochloric acid as a reaction product. Consequently, such materials should not be added directly to calcium hypochlorite since they are not "calcium hypochlorite-compatible".

Non-limiting examples of organo-silicon materials that may be used as a hydrophobizing reagent include: diethyl dichlorosilane, methylphenyl dichlorosilane, phenylethyl diethoxysilane, 3,3,3-trifluoropropylmethyl dichlorosilane, trimethylbutoxy silane, sym-diphenyltetramethyl disiloxane, octamethyl trisiloxane, octamethyl cyclotetrasiloxane, hexamethyl disiloxane, pentylmethyl dichlorosilane, trimethyl chlorosilane, trimethyl methoxysilane, trimethyl ethoxysilane, methyl trichlorosilane, methyl trimethoxysilane, methyl triethoxysilane, hexamethyl cyclotrisiloxane, hexamethyldisiloxane, hexaethyldisiloxane, dimethyl chlorosilane, dimethyl dichlorosilane, dimethyl dimethoxysilane, dimethyl diethoxysilane, polydimethylsiloxanes comprising 3 to 200 dimethylsiloxy units, trimethylsiloxy or hydroxydimethylsiloxy end blocked poly(dimethylsiloxane) polymers (silicone oils) having an apparent viscosity within the range of from 1 to 1,000 mPascals at 25° C., vinyl silane, gamma-methacryloxypropyl trimethoxy silane, polysiloxanes, e.g., polysiloxane microspheres, and mixtures of such organo-silicone materials.

Silicone oils are well known commercial materials. Molecular weights of silicone oils may vary. In alternate non-limiting embodiments, the number average molecular weight ($M_n$) of silicone oils may range from 150 to 450,000, such as from 200 to 100,000, e.g., 400 to 15,000.

Non-limiting examples of organo-silicon compounds represented by general formula IV, particularly when $R^3$ is methyl, are the methyl silsesquioxane resins (CAS 68554-70-1) that are available from GE Silicones as Tospearl® silicone resins. The foregoing GE methyl silsesquioxane resins are spherical white powders having an average particle size of from 0.5 to 12 microns, a specific surface area of from 20 to 30 m²/gram, an oil (linseed) absorption of from approximately 58 to 75 mL/100 g, and a pH of approximately 7 (2% dispersed in a 1:1 methanol:water solution). Methyl silsesquioxane resins may have linear, ladder or polycyclic structures.

Polysiloxane microspheres, e.g., polyalkylsilsesquioxanes, such as polymethylsilsesquioxanes, may be prepared by forming a first aqueous mixture comprising an anionic surfactant, e.g., disodium lauryl phenol ether disulfonate, a polymeric stabilizer, e.g., poly(vinyl pyrrolidone), and hydroxide base, e.g., an alkali metal hydroxide or ammonium hydroxide; adding alkoxy silane monomer, e.g., methyltrimethoxysilane, to the first aqueous mixture to form a second aqueous mixture; stirring the second aqueous mixture at a temperature of from 5° C. to 90° C. for at least 1 hour; separating polysiloxane microspheres from the second aqueous mixture; and optionally washing the microspheres with water, drying the washed microspheres and jet treating/milling the dry microspheres. See, for example, the disclosures found in U.S. Pat. No. 5,801,262, column 1, line 55 to column 3, line 67, and in U.S. Pat. No. 5,936,031, column 1, line 50 to column 3, line 18, which disclosures are incorporated herein by reference. Ladder-like silicone polymers, e.g., polyalkylsilsesquioxanes, are described in U.S. Patent publication 2003/0212228 A1 at paragraphs [0018] to [0136], which disclosure is incorporated herein by reference.

Non-limiting examples of organo-titanium compounds include: tetra($C_1$-$C_{18}$) alkoxytitanates, methyl trimethoxy titanium, methyl triisopropoxy titanium, methyl tributoxy titanium, tri-t-butoxy isopropyl titanium, tributoxy butyl titanium, triethoxy butyl titanium, tributoxy phenyl titanium, triisopropoxy phenyl titanium, and triisobutoxy phenyl titanium.

Non-limiting examples of organo-zirconium compounds include tetra($C_1$-$C_{18}$) alkoxy zirconates, phenyl zirconium trichloride, methyl zirconium trichloride, ethyl zirconium trichloride, propyl zirconium trichloride, methyl zirconium tribromide, ethyl zirconium tribromide, propyl zirconium tribromide, chlorotripentyl zirconium, and mixtures of such organo-zirconium compounds. Zirconium compounds similar in structure to the titanium compounds described herein (except for substituting zirconium for titanium) may also be used.

In a further non-limiting embodiment, the hydrophobic additive may comprise a solid carrier that has been treated, e.g., coated, with a hydrophobizing reagent (agent). For example, a solid carrier, e.g., a metal oxide such as an inorganic metal oxide, can be treated with one or more hydrophobizing agents and the resulting treated solid carrier blended with solid, e.g., particulate, calcium hypochlorite. The amount of hydrophobizing reagent used to treat the solid carrier is that amount that is sufficient to yield a composition comprising the mixture of treated carrier and solid calcium hypochlorite that has reduced hydrophilic properties, e.g., a composition having a solution rate in water that is lower than the solution rate of the calcium hypochlorite used to prepare the composition. In a non-limiting embodiment, the weight ratio of hydrophobizing reagent to carrier may range from 1:1 to 1:20, e.g., from 1:3 to 1:6. Expressed differently, from 5 to 50 parts, e.g., 5 to 25 or 5 to 15 parts of hydrophobizing reagent may be blending with 100 parts of solid carrier.

In a further non-limiting embodiment of the present invention, the amount of hydrophobizing agent used to treat the solid carrier is that amount that is sufficient to provide a treated carrier that has a methanol wettability of at least 10 percent. In alternate non-limiting embodiments of the present invention, the treated carrier has a methanol wettability of at least 20 percent, e.g., 25 percent. In other non-limiting embodiments of the present invention, the treated carrier has a methanol wettability of at least 30 percent, e.g., at least 40 percent. The methanol wettability of the treated carrier may be less than 70 percent, such as less than 60 percent, e.g., 40 to 50 percent.

The methanol wettability value is the concentration of methanol (in weight percent) required to wet 50 percent of the treated carrier, i.e., the amount of methanol needed to produce 50 percent wetting (50 percent suspended at the top of the liquid layer and 50 percent in the sediment) in the methanol wettability test, which is described herein.

Methanol wettability is determined by first determining the amount of treated carrier wetted with 50 weight percent methanol. This is done by adding 2.0 grams of a sample to a 50 milliliter (mL) conical centrifuge tube containing 15 mL of a 50 weight percent mixture of methanol (HPLC grade) and deionized water. A centrifuge tube that is graduated in 0.5 mL marks up to the 10 mL level and in 1.0 mL marks from the 10 to 50 ml levels is used. The contents of the tube are shaken for 15 seconds and centrifuged at approximately 4,000 revolutions per minute (rpm) in a hanging bucket type centrifuge at room temperature (23-25° C.) for 15 minutes. The centrifuge tube is removed and handled carefully to avoid re-suspending the sediment. The amount of treated carrier that is wetted, i.e., formed the sediment, is recorded to the nearest 0.5 mL.

Afterwards, a series of at least 3 different concentrations of the methanol/water mixture are tested. This is done to determine the concentration of methanol that will cause 50 and 100 percent wetting of the treated carrier. Desirably, the concentrations selected include at least one concentration above and at least one below the amount necessary to cause 50 percent of the treated carrier to be wetted. The concentrations selected may range from 5 to 95 weight percent methanol, in 5 weight percent increments, depending on the amount wetted by 50 weight percent aqueous methanol. For example, if the treated carrier is wetted with 50 weight percent methanol, concentrations of methanol ranging from 5 to 45 weight percent would be tested.

The percent of treated carrier wetted by the different concentrations of methanol is calculated by dividing the volume of the partially wetted treated carrier by the volume of the completely wetted treated carrier and multiplying by 100. The results are plotted on a graph of Percent Wetted versus Concentration of Methanol and fitted with a straight line. The concentration of methanol at which 50 percent of the treated carrier is wetted is determined from the line equation.

In a non-limiting embodiment of the present invention, the solid carrier may be a naturally occurring or synthetic calcium hypochlorite-compatible inorganic oxide (or mixture of inorganic oxides) or clay-like mineral (natural or synthetic) that have either oxygen (chemisorbed or covalently bonded) or hydroxyl (bound or free) on the exposed surface of the solid inorganic oxide, thereby allowing the surface of the solid inorganic oxide to bind, e.g., by covalent bonding, with the hydrophobizing agent. The solid carrier is desirably a particulate material having a particle size that can be similar to but is generally smaller than the particle size of the calcium hypochlorite with which it is commingled.

Non-limiting examples of inorganic oxide carriers include the oxides of metals in Periods 2, 3 and 4 of Groups IIIA, IVA (except carbon) and IVB of the Periodic Classification of the Elements (General Chemistry by Theodore L. Brown, 1963, Charles E. Merrill Books, Inc., Columbus Ohio). For purposes of this disclosure, silicon is considered to be a metal.

Specific examples of such inorganic oxide carriers include, but are not limited to, aluminum oxide, aluminum hydroxide, boron oxides, zirconium oxide, zirconium hydroxide, titanium oxide, titanium hydroxide and silicon oxides, e.g., precipitated silicas, pyrogenic (fumed) silicas and colloidal silicas (silica gels).

Non-limiting examples of clays and clay-like minerals that may be used as a solid carrier for a hydrophobic agent include the hydrous silicates of aluminum, magnesium and calcium (naturally occurring or synthetic). In particular, there can be mentioned the amorphous (to x-ray) clay minerals, e.g., allophone and evansite, and crystalline clay minerals, e.g., clays classified into groups such as the kaolin group, the montmorillonite group, the illite or mica group, the chlorite group, the vermiculite group, the palygorskite group (including attapulgite), glauconite and sepiolite. Magnesium silicate materials include talc and talc-like materials. Calcium silicate materials include Wollastonite.

Aluminum silicates can be described as natural or synthetic materials where the silicon atoms of silicon dioxide are partially replaced, or substituted, either naturally or synthetically, by aluminum atoms. For example, 5 to 90, alternatively 10 to 80, percent of the silicon atoms of silicon dioxide are replaced by aluminum atoms to yield aluminosilicates. Non-limiting examples of aluminosilicates include: Muscovite, Beryl, Dichroite, Sepiolite, Bentonite, Attapulgite, Montmorillonite and Kaolinite. As used herein, the term aluminosilicates is intended to include mica and mica-like minerals. Non-limiting examples of synthetic aluminosilicates include Zeolite and those materials that may be represented by formulas such as for example $[(Al_2O_3)_x(SiO2)_y.(H_2O)_z]$; or $[(Al_2O_3)_x(SiO2)_y YO]$, wherein Y is magnesium or calcium. The natural aluminum silicate clay minerals may be milled to a desired particle size.

Silicon oxides such as precipitated silicas, pyrogenic silicas and colloidal silicas are commercially available and are well known to those skilled in the art. For example, silicon oxide materials are sold commercially by PPG Industries, Inc. under the Hi-Sil, Flo-Gard, and Lo-Vel trademarks. Non-limiting examples of such silicon oxide materials are those having grade designations such as Hi-Sil® 210, 233, 243, 315, ABS, 190, 255, SP, T-700 and 2000. Other examples of silicon oxide materials include those available from Rhodia Corp. having the grade designations Z1165 MP and Z1165 GR; and silicon oxide materials available from Degussa AG as Ultrasil® VN-2, VN-3, and Aerosil® 812, 972, 974, etc. In a non-limiting embodiment, the silicon oxide is precipitated silica [CAS 112926-00-8].

In accordance with a non-limiting embodiment of the present invention, the BET surface area (single point) of precipitated silica used as the solid carrier may vary from 40 square meters/gram ($m^2$/g) to 1000 $m^2$/g, such as from 50 to 500 $m^2$/g, e.g., from 70 to 350 $m^2$/g. The pH of precipitated silica may range from 5 to 9, e.g., 6.5 to 7.5, (5% suspension in 50/50 ethanol/water mixture).

The hydrophobic additive comprising a carrier and hydrophobizing reagent can be prepared by treating the surface of the carrier, e.g., inorganic metal oxide, with the hydrophobizing reagent, e.g., an organo-silane, by methods known to those skilled in the art. For example, dry particulate precipitated silica can be treated with an organo-silane by spraying the hydrophobizing agent, e.g., a silicone oil, onto a bed of agitated precipitated silica. Alternatively, the carrier can be treated while suspended in aqueous or organic solvent, such as in the manner disclosed in U.S. Pat. No. 5,908,660 (column 2, line 40 to column 6, line 10), and U.S. Pat. No. 5,919,298 (column 2, line 42 to column 6, line 34), which disclosures are incorporated herein by reference. Although the foregoing described methods are directed to treating precipitated silica with organo-silanes, the steps used in such methods may be used in treating other metal oxides (as defined herein) with other hydrophobizing reagents (as described herein).

Non-limiting examples of clay minerals that have been treated with hydrophobizing reagent that may be used as the hydrophobic additive include hydrophobic clays available from Engelhard, e.g., Translink® 37 and 77 hydrophobic clays, and Starfil PH hydrophobic clay available from Kentucky-Tennessee Clay Co.

In a non-limiting embodiment, preparation of the hydrophobic additive comprising a carrier and hydrophobizing agent can include heating of the treated carrier to enhance the bonding of the hydrophobizing agent to the surface of the carrier. Temperatures to which the treated carrier can be heated may vary depending on the carrier and the hydrophobizing agent. Temperatures should however not exceed a temperature at which either the carrier or hydrophobizing agent is substantially altered. In a non-limiting embodiment, such temperatures may range from ambient room temperature, e.g., 20° C., to 300° C. In alternate non-limiting embodiments, such temperatures may range from 100° C. to 300° C., e.g., from 105° C., to 270° C. In an embodiment wherein alkoxy silanes are used as the hydrophobizing agent, heat treatment temperatures may range from 130° C., to 150° C.; while in an embodiment wherein silicone oils are used as the hydrophobizing agent, heat treatment temperatures may range from 100° C. to 300° C.; such temperature being dependent often on the time allowed for the hydrophobizing treatment to occur. The temperature at which heat treatment of the hydrophobizing agent treated carrier is performed may vary between any of previously stated temperatures, including the specifically recited temperatures.

Heat treatment of hydrophobizing agent treated carriers, e.g., inorganic metal oxides, are conducted for a time sufficient to enhance the bonding of the hydrophobizing agent to the surface of the carrier, e.g., enhance covalent bonding between the hydrophobizing agent and the surface of the carrier. The period of time required for such heat treatment may vary, and will depend on factors that include, but are not limited to, the temperature of heat treatment, whether catalysts are used, and whether the heat treatment process is a batch or continuous process. In a non-limiting embodiment, the period of heat treatment may range from 0.01 to 17 hours or longer, e.g., from 5 to 7 hours.

Commingling (blending) of the hydrophobic additive, e.g., hydrophobizing reagent or inorganic metal oxide carrier treated with hydrophobizing reagent, and calcium hypochlorite may be accomplished by mixing the two materials in a vessel used to blend a liquid material and a solid material, or two solid materials (as the case may be), e.g., a batch blender or double cone blender. In a non-limiting embodiment, the calcium hypochlorite is a particulate material, e.g., granular or powdery in form, and the hydrophobic additive is a liquid hydrophobizing reagent. In that case, the liquid hydrophobic additive can be sprayed onto solid calcium hypochlorite while it is being agitated, e.g., by spraying the liquid additive onto a fluid bed of the calcium hypochlorite. In another non-limiting embodiment, the calcium hypochlorite is granular or powdery in form and the hydrophobic additive is a carrier, e.g., particulate metal oxide, such as an inorganic metal oxide, that has been treated with hydrophobizing agent, e.g., organo-silane treated precipitated silica.

In a non-limiting embodiment, the particulate hydrophobic additive has a particle size that is sufficiently fine to form a thin coating on at least a portion (if not substantially all) of the calcium hypochlorite when it is blended with particulate calcium hypochlorite. In accordance with a non-limiting embodiment, a sufficient amount of the calcium hypochlorite is coated with hydrophobic additive to diminish the hydrophilic properties of the calcium hypochlorite, e.g., decrease the solution rate in water of the calcium hypochlorite to a desired value.

The temperature and time for blending of the calcium hypochlorite and hydrophobic additive materials may vary. The time required for the blending operation will depend on the particle size of the calcium hypochlorite and the particle size or other physical state of the hydrophobic additive, e.g., whether the hydrophobic additive is a liquid or a solid. Generally, blending of such materials is performed at temperatures at which there is little or no loss of free available chlorine from the calcium hypochlorite. In a non-limiting embodiment, the materials are blended at ambient temperatures (although temperatures slightly above ambient may be used if loss of FAC from the calcium hypochlorite is avoided, or if the FAC loss can be tolerated). The time required for the blending operation is that time that is sufficient to allow the hydrophobic additive to be distributed onto the surface of the calcium hypochlorite. In alternate non-limiting embodiments, the blending operation is performed over a period ranging from 15 minutes to several hours, e.g., from 30 minutes to 2 hours.

In a non-limiting embodiment, blending or mixing of the solid calcium hypochlorite, e.g., granular calcium hypochlorite, with the hydrophobic additive may involve a surface phenomenon in which the hydrophobic additive coats at least a portion of the surface of the calcium hypochlorite and thereby provides the solid calcium hypochlorite with reduced hydrophilic properties, which has the effect of lowering the solution rate in water of the calcium hypochlorite. Enough of the surface of the calcium hypochlorite is coated so as to obtain a desired solution rate. In a non-limiting embodiment, only that amount of hydrophobic additive that is sufficient to accomplish the foregoing object is used, i.e., the calcium hypochlorite is provided with reduced hydrophilic properties by means of a relatively small amount of oxidizable organic matter. Consequently, blending of the calcium hypochlorite with the hydrophobic additive produces a profound change in the surface character of the calcium hypochlorite while at the same time causing a minimum change in the total surface area or internal properties of the calcium hypochlorite.

As indicated, the amount of hydrophobic additive blended with calcium hypochlorite may vary. However, the amount of hydrophobic additive used is chosen so as not to adversely affect the forming of the calcium hypochlorite composition into shapes that are sold commercially, e.g., tablets and pellets, in the case where a solid enlargement forming process is employed. In a non-limiting example, when the hydrophobic additive is in the form of inorganic metal oxide, e.g., precipitated silica, treated with hydrophobizing agent, e.g., silicone oil, the amount of hydrophobic additive that is blended with the granular calcium hypochlorite to form a tableting mixture is generally in the range of from 0.1 to 0.45 weight percent, based on the total weight of the tableting mixture.

The calcium hypochlorite compositions of the present invention may also contain additives, e.g., adjuvants that do not adversely affect the sanitizing effectiveness of the composition. In a non-limiting embodiment, when for example compositions of the present invention are formed into solid shaped articles, e.g., tablets, adjuvant additives that may be present include, but are not limited to, conventional binders and buffering agents. Other additives that may be present when the composition is in either tablet or granular form include, but are not limited to, chemically compatible scale inhibitors, and colorant-containing inorganic salts, such as those described in U.S. Pat. No. 5,049,385, at column 5, line 62 through column 7, line 8, which disclosure is incorporated herein by reference.

Inert inorganic diluent additives may also be added to the calcium hypochlorite compositions of the present invention. Non-limiting examples of inert, inorganic solid diluent materials include sodium chloride, potassium chloride, lithium chloride, calcium chloride, calcium oxide, calcium hydroxide, magnesium hydroxide, aluminum hydroxide, sodium sulfate, magnesium sulfate, magnesium silicate (talc) and mixtures of such inorganic inert materials. In a non-limiting embodiment, pH neutral salts are used. By inert is meant that the inorganic material does not affect substantially the shelf life of the calcium hypochlorite, or the SADT (self accelerating decomposition temperature) of the calcium hypochlorite. In a non-limiting embodiment, the inert inorganic diluent additive is anhydrous; however, it may contain water of hydration, e.g., hydrated magnesium sulfate.

The amount of adjuvant additives, including added inert, inorganic diluent materials, present within the calcium hypochlorite compositions of the present invention may vary. In a non-limiting embodiment, such additives may be present in amounts, for example, that range from 0.001% to 15% by weight, alternatively from 0.01% to 12 percent by weight, e.g., from 0.1 to 5% by weight, based on the total weight of the composition. The amount that each of such additives that may be added to the calcium hypochlorite compositions of the present invention may comprise a range that may vary between any of the aforementioned recited values. For example, non-limiting examples of such additives and their amounts include, but are not limited to, sodium tripolyphosphate, which in one non-limiting embodiment may be present in amounts of from 1 to 5, e.g., 3 weight percent; and added inert salts, e.g., sodium chloride, which in one non-limiting embodiment can be present in amounts of from 8 to 15, e.g., 10 to 12, weight percent.

In a non-limiting embodiment of the present invention, hydrated lime (calcium hydroxide), magnesium hydroxide, aluminum hydroxide and/or magnesium silicate can be added to the calcium hypochlorite composition. When the calcium hypochlorite compositions of the present invention are used for the treatment of residential waste water, hydrated lime is particularly desirable as an additive. In such applications, the amount of added hydrated lime may in one non-limiting embodiment range from 0.5 to 5 weight percent, such as from 1 to 2.5 weight percent.

The calcium hypochlorite compositions of the present invention, usually in the form of granules, pellets or tablets, can be added directly to an aqueous medium to be treated, e.g., sanitized, or can be added to any suitable chlorination (feeder) equipment or device, i.e., feeder units used to prepare an aqueous solution of calcium hypochlorite, which solution in turn is used to sanitize an aqueous medium requiring such treatment, e.g., a swimming pool, hot tub or spa, or waste water stream. Non-limiting examples of such chlorination devices are those depicted in FIG. 1 of U.S. Pat. No. 5,384, 102, FIG. 1 of U.S. Pat. No. 5,427,748 and FIG. 1 of U.S. Pat. No. 6,298,871 B1, which figures and the supporting disclosures of the structures of the chlorination devices are incorporated herein by reference.

The calcium hypochlorite compositions of the present invention can be used for the treatment of standing and recirculating water systems, such as cooling towers, evaporative condensers, air washers, swimming pools, hot tubs, spas, etc, for the treatment of residential waste water, and for the preparation of aqueous calcium hypochlorite solutions used for sanitizing food and the surfaces and equipment used in the processing of food products (raw and processed). When used to sanitize the surface of an article, the sanitized water can be applied to such a surface by any appropriate method, examples of which include but are not limited to, spray application; wiping with soaked rags; curtain or waterfall application; and soaking by immersion.

Compositions of the present invention can be formed into solid shaped articles, including but not limited to, tablets, bricks, briquettes, pellets, etc, by conventional size enlargement equipment. Examples of such equipment include, but are not limited to, molding presses, tableting presses, roll-type presses, pellet mills and screw extruders. In alternate non-limiting embodiments, the solid shaped article may have a mass of between 1 gram and 350 grams or more, e.g., between 7 and 300 grams, more particularly between 140 grams and 300 to 350 grams. The size of the solid shaped article may vary widely and is determined by the intended application, such as the internal dimensions and operating parameters of the chlorination unit in which the solid shaped article is to be used, and/or conventional commercial handling and packaging units.

In the case of a solid shaped article that is in the shape of a tablet having a mass of, for example, from 140 to 350 grams, the diameter of the tablet in one non-limiting embodiment may be between 6.7 centimeters (cm) (2.625 inches) and 8.9 cm (3.5 inches), e.g., between 7.9 cm (3.125 inches) and 8.3 cm (3.25 inches), and have a thickness of from 2.5 cm (1 inch) to 5.1 cm (2 inches), e.g., 3.2 cm (1.25 inches). The dimensions of such tablets may vary within a range that may vary between any of the recited values.

In a non-limiting embodiment, granular calcium hypochlorite of the compositions of the present invention have a size distribution predominantly between 45 mesh and 10 mesh ASTM E11 ASD, e.g., the granules are principally between on average 0.36 mm (0.014 inches) and 2.00 mm (0.08 inches), is used to produce solid shaped articles such as tablets. Particles smaller than 50 mesh ASTM E11 ASD, e.g., 0.30 mm (0.012 inches), that are present in the granular calcium hypochlorite generally represent a minor percentage, usually less than 2 percent, of the material charged to a size enlargement device.

The present invention is more particularly described in the examples that follow, which are intended to be illustrative only, since numerous modifications and variations therein will be apparent to those skilled in the art. In the following examples, unless otherwise specified, all parts and percentages are by weight.

EXAMPLE 1

A. Preparation of Hydrophobic Precipitated Silica

Hi-Sil® ABS (CAS 112926-00-8) amorphous precipitated silica (PPG Industries, Inc.) having approximately 5 percent water, a pH of approximately 7 (5% suspension in water), an oil absorption (dibutyl phthalate) of 305 mL/100 grams, and a BET surface area (single point) of approximately 150 square meters/gram was treated in the following manner. 100 parts of the precipitated silica having a median particle size of approximately 25 microns were placed in a closed jacketed mix tank. The tank was purged with nitrogen. Approximately 15 parts per 100 parts of precipitated silica of dimethylpolysiloxane (CAS #63148-62-9, SF18-350 from GE Silicones having a number average molecular weight of approximately 13,700) was sprayed onto the silica while it was being agitated, and the mixture heated under a nitrogen atmosphere for approximately 5 to 7 hours at approximately 290° C. (550° F.). The resultant treated precipitated silica, which contained approximately 13% of the dimethylpolysiloxane, was cooled to room temperature. The bulk density of the treated silica was approximately 9 pounds/ft$^3$ (144 kg/m$^3$).

B. Blending of the Hydrophobic Precipitated Silica with Calcium Hypochlorite

Granular calcium hypochlorite of approximately 73 percent available chlorine assay and a median particle size of approximately 800 microns was blended with various amounts of the dimethylpolysiloxane-treated precipitated silica, and each of the blends was formed into tablets having a diameter of approximately 3⅛ inches (7.9 cm). The density of the tablets was approximately 1.92. For comparison, tablets were also formed from the granular calcium hypochlorite used to prepare the blends of calcium hypochlorite and dimethylpolysiloxane-treated precipitated silica. The density of these tablets was also approximately 1.92.

C. Testing of the Solution Rate in Water of the Tablets Prepared in B

A feeder apparatus of the type shown in FIG. 1 of U.S. Pat. No. 5,427,748 was used to test the solution rate of the calcium hypochlorite tablets prepared in Part B. For each test, 19 calcium hypochlorite tablets (prepared as in B above) were placed flat in a single layer on top of the sieve plate (reference number 22) of the apparatus described in the '748 patent. Water was introduced into the apparatus described in the '748 patent through a conduit (reference number 40) at a flow rate of five gallons/minute (18.9 liters/minute) for two hours. The water had a temperature of 68° F. (20° C.). Results are tabulated in Table 1.

TABLE 1

| | Tablet Dissolve Rate[2] | | |
|---|---|---|---|
| % Hydrophobic Silica[1] | First Hour | Second Hour | 2 Hour Average |
| 0 | 0.84 | 0.53 | 0.69 |
| 0.2 | 0.47 | 0.26 | 0.37 |
| 0.3 | 0.41 | 0.2 | 0.31 |
| 0.4 | 0.38 | 0.19 | 0.29 |

[1]Amorphous Precipitated Silica Treated with 13% Dimethylpolysiloxane
[2]Pounds/Hour of Chlorine Delivery Rate

EXAMPLE 2

The procedures of Example 1 were repeated with a different lot of the granular calcium hypochlorite used in Example 1, and a different lot of the Hi-Sil® ABS amorphous precipitated silica used in Example 1. Test results are tabulated in Table 2.

TABLE 2

| | Tablet Dissolve Rate[2] | | |
|---|---|---|---|
| % Hydrophobic Silica[1] | First Hour | Second Hour | 2 Hour Average |
| 0 | 0.76 | 0.5 | 0.63 |
| 0.45 | 0.23 | 0.11 | 0.17 |

[1]Amorphous Precipitated Silica Treated with 13% Dimethylpolysiloxane
[2]Pounds/Hour of Chlorine Delivery Rate The data of Tables 1 and 2 show that there is a measurable slowing of the solution rate of calcium hypochlorite tablets containing hydrophobic precipitated silica compared to calcium hypochlorite tablets without the hydrophobic precipitated silica. The data shows also that the higher the amount of hydrophobic precipitated silica blended with the calcium hypochlorite, the lower is the delivery rate. The data further show that the chlorine delivery rate is higher during the first hour of operation than during the second hour of operation. Typically, delivery rates for calcium hypochlorite tablets start out at one level and then decrease during the first hour or two of operation before leveling off at some fraction of the initial rate.

EXAMPLE 3

The tablets of Example 1 were analyzed for hydrophobicity by way of water contact angle measurement. Test results are tabulated in Table 3.

TABLE 3

| | Water Contact Angle[2] | |
|---|---|---|
| % Hydrophobic Silica[1] | At 5 seconds | At 20 seconds |
| 0 | 30° ± 16% | 28° ± 15% |
| 0.2 | 67° ± 23% | 63° ± 24% |
| 0.3 | 66° ± 18% | 61° ± 18% |
| 0.4 | 80° ± 19% | 76° ± 16% |

[1]Amorphous Precipitated Silica Treated with 13% Dimethylpolysiloxane
[2]0.5 microliter droplet of deionized water with a surface tension of 72 ± 2 dynes/cm.

The data of Table 3 show that the addition of hydrophobic silica to calcium hypochlorite results in tablets that are less easily wetted by water, the tablets having steeper water contact angles.

Although the present invention has been described with reference to specific details of certain embodiments thereof, it is not intended that such details should be regarded as limitations upon the scope of the invention except insofar as they are included in the accompanying claims.

What is claimed is:

1. A composition comprising a mixture of:
   (i) a major amount of solid calcium hypochlorite, and
   (ii) an amount of hydrophobic additive that is sufficient to provide a calcium hypochlorite composition having reduced hydrophilic properties, said composition being substantially free of discrete particulate Group IIA and IIIA metal stearate, said hydrophobic additive being a particulate calcium hypochlorite-compatible carrier material chosen from inorganic metal oxide and clay material, the surface of which has been treated with hydrophobizing agent represented by one of the following general formulae, $$R^1_a MX_{4-a} \quad \text{I}$$

$$R^2_{2n+2} Si_n O_{n-1} \quad \text{II}$$

$$R^1_{2m} Si_m O_m \quad \text{III}$$

$$(R^3 Si)_{2p} O_{3p} \quad \text{IV}$$

wherein (a) M is independently chosen from silicon, titanium or zirconium; (b) each $R^1$ is independently chosen from a saturated hydrocarbon group containing from 1 to 18 carbon atoms; (c) each X is independently chosen from alkoxy containing from 1 to 12 carbon atoms, or acyloxy containing from 1 to 12 carbon atoms; (d) a is a number chosen from 1 to 4, (e) each $R^2$ is independently chosen from halo, hydroxy, or $R^1$ with the proviso that at least 50 mole percent of the $R^2$ substituents are saturated hydrocarbon groups; (f) n is a number of from 2 to 10,000; (g) m is a number of from 3 to 20, (h) $R^3$ is chosen from an aliphatic, cycloaliphatic or aryl hydrocarbon containing from 1 to 6 carbon atoms, cyclohexyl, vinyl or phenyl, or a glycidoxy alkyl group, and (i) p is a number chosen from 4 to 1000, the weight ratio of hydrophobizing agent to carrier material being from 1:1 to 1:20.

2. The composition of claim 1 wherein the solution rate in water of the calcium hypochlorite composition is less than the solution rate of the calcium hypochlorite used to prepare the composition.

3. The composition of claim 2 wherein the hydrophobic additive present in the composition ranges from 0.1 to 5 weight percent, based on the total weight of the composition.

4. The composition of claim 1 wherein the hydrophobizing agent is chosen from organo-silane materials or organo-siloxane materials.

5. The composition of claim 4 wherein the inorganic metal oxide is an oxide of a metal chosen from the metals in Periods 2, 3 or 4 of Groups IIIA, IVA (except carbon) and IVB of the Periodic Classification of the Elements, and the clay material is a hydrous silicate of aluminum, magnesium or calcium.

6. The composition of claim 5 wherein the inorganic metal oxide is chosen from the oxides of boron, aluminum, silicon, titanium or zirconium.

7. The composition of claim 5 wherein the inorganic metal oxide is precipitated silica.

8. The composition of claim 7 wherein the precipitated silica is treated with an organo-siloxane.

9. The composition of claim 8 wherein the organo-siloxane treated precipitated silica represents from 0.1 to 2 weight percent of the composition.

10. The composition of claim 9 wherein the composition is in the form of a tablet.

11. The composition of claim 10 wherein the calcium hypochlorite of the composition has a free available chlorine content that ranges from 45 to 80 percent.

12. The composition of claim 11 further comprising from 2 to 2.5 weight percent of added calcium hydroxide, magnesium hydroxide, aluminum hydroxide or magnesium silicate, based on the total weight of the composition.

13. The composition of claim 1 wherein the mixture comprises at least 75 weight percent of hydrated calcium hypochlorite and not more than 2 weight percent of hydrophobic additive, said hydrophobic additive being a particulate calcium hypochlorite-compatible silicon oxide carrier material, the surface of which has been treated with organo-silicon hydrophobizing agent, the weight ratio of hydrophobizing agent to silicon oxide carrier being from 1:3 to 1:6.

14. The composition of claim 13 wherein the solution rate of the composition in water is diminished to not more than 50 to 70 percent of the hydrated calcium hypochlorite.

15. The composition of claim 13 wherein the composition comprises at least 90 weight percent of hydrated calcium hypochlorite.

16. The composition of claim 13 wherein the particulate silicon oxide carrier material is precipitated silica.

17. The composition of claim 16 wherein the organo-silicon material is chosen from silicon oil having a number average molecular weight of from 150 to 450,000 or polyalkylsilsesquioxane.

18. The composition of claim 17 wherein the organo silicon material is a silicon oil having a number average molecular weight of from 400 to 15,000, and the polyalkylsilesquioxane is polymethylsilsesquioxane.

19. The composition of claim 18 wherein the precipitated silica is treated with organo polysiloxane.

20. The composition of claim 19 wherein the composition is in the form of a tablet.

* * * * *